US009808347B2

(12) United States Patent
Bailey et al.

(10) Patent No.: US 9,808,347 B2
(45) Date of Patent: Nov. 7, 2017

(54) LINER SYSTEM

(71) Applicant: Biomet Manufacturing, LLC, Warsaw, IN (US)

(72) Inventors: Kirk J. Bailey, Rochester, IN (US); Aaron P. Smith, Warsaw, IN (US); W. Jason Slone, Silver Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/592,367

(22) Filed: Jan. 8, 2015

(65) Prior Publication Data
US 2016/0199188 A1    Jul. 14, 2016

(51) Int. Cl.
*A61F 2/32*      (2006.01)
*A61F 2/34*      (2006.01)
*A61F 2/30*      (2006.01)
*A61F 2/36*      (2006.01)

(52) U.S. Cl.
CPC ...... *A61F 2/34* (2013.01); *A61F 2002/30332* (2013.01); *A61F 2002/30616* (2013.01); *A61F 2002/30822* (2013.01); *A61F 2002/325* (2013.01); *A61F 2002/3233* (2013.01); *A61F 2002/3241* (2013.01); *A61F 2002/3266* (2013.01); *A61F 2002/3438* (2013.01); *A61F 2002/3493* (2013.01); *A61F 2002/3611* (2013.01)

(58) Field of Classification Search
CPC ................ A61F 2/34; A61F 2002/3493; A61F 2002/3208; A61F 2002/325; A61F 2002/3258; A61F 2002/3298; A61F 2002/3631
See application file for complete search history.

(56) References Cited

U.S. PATENT DOCUMENTS

| 3,813,699 | A | * | 6/1974 | Giliberty | A61F 2/32 |
| | | | | | 623/22.17 |
| 3,818,512 | A | | 6/1974 | Shersher | |
| 4,770,658 | A | * | 9/1988 | Geremakis | A61F 2/32 |
| | | | | | 623/22.19 |
| 5,824,108 | A | * | 10/1998 | Huebner | A61F 2/32 |
| | | | | | 623/22.29 |
| 2004/0204767 | A1 | | 10/2004 | Park et al. | |
| 2006/0217815 | A1 | | 9/2006 | Gibbs et al. | |

OTHER PUBLICATIONS

"International Application Serial No. PCT/US2016/012279, International Search Report dated Feb. 29, 2016", 6 pgs.
"International Application Serial No. PCT/US2016/012279, Written Opinion dated Feb. 29, 2016", 7 pgs.
"International Application Serial No. PCT/US2016/012279, International Preliminary Report on Patentability dated Jul. 20, 2017", 9 pgs.

* cited by examiner

*Primary Examiner* — Brian Dukert
(74) *Attorney, Agent, or Firm* — Schwegman Lundberg & Woessner, P.A.

(57) ABSTRACT

A prosthesis according to the present disclosure includes a shell. A liner is disposed within the shell, and a femoral head may be disposed within the liner. A locking mechanism may assist in securing the liner within the shell. The locking mechanism may be removed when the shell, liner, and femoral head are implanted. The shell extends beyond a hemisphere of the shell, and the liner extends beyond a hemisphere of the liner.

22 Claims, 11 Drawing Sheets

LINER SYSTEM

FIELD

The present disclosure relates to replacement devices, including a constrained joint having an acetabular shell liner.

BACKGROUND

This section provides background information related to the present disclosure and is not necessarily prior art.

Articulating regions of an anatomy can include areas where two bone sections move relative to one another. For example, an acetabulum can provide a region for articulation with a femoral head. The articulating region, however, can become injured, worn, or suffer from a condition such as arthritis. As a remedy, joint portions can be replaced with various prostheses. Such prostheses can replace the acetabulum, the femoral head, and various other portions of the femur, or selected combinations thereof.

Several types of joint prosthetics are generally known in the art. A constrained prosthetic may be used when dislocation is a constant or repeated issue. The constrained prosthetic provides a ball and prosthetic socket where the ball of the prosthetic is held within the prosthetic socket or an internal cavity of the prosthetic by a mechanical means. For example, a metal ring may be placed around the opening of a liner portion disposed in the prosthetic socket to hold the ball of the joint prosthetic within the liner portion. The ring increases the lever out force needed to remove the ball from the liner portion. This makes dislocation of the ball portion from the liner portion less likely. The ring may either be assembled onto the liner portion during the manufacturing process or the ring may be installed during the operative procedure. Generally, however, if the ring is to be installed during the operative procedure, the liner portion must include deflectable portions, such as separated by slits, to allow the physician to install the ring.

SUMMARY

This section provides a general summary of the disclosure, and is not a comprehensive disclosure of its full scope or all of its features.

A prosthesis according to the present disclosure may include a shell. A liner may be disposed within the shell, and a femoral head may be disposed within the liner. A locking mechanism may secure the liner within the shell. The locking mechanism may be removed when the shell, liner, and femoral head are implanted. The shell may have a surface that extends beyond a hemisphere, and the liner may have a surface that extends beyond a hemisphere.

The shell of the prosthesis according to the present disclosure may further include a peripheral surface. A diameter of the peripheral surface may be less than a diameter of the hemisphere of the shell.

The liner of the prosthesis according to the present disclosure may further include a rounded edge. A diameter of the rounded edge may be less than a diameter of the hemisphere of the liner.

The prosthesis according to the present disclosure may further include the diameter of the peripheral surface being less than the diameter of the hemisphere of the liner.

The prosthesis according to the present disclosure may further include the shell being formed of a biocompatible metal and the liner being formed of a polymer.

The prosthesis according to the present disclosure may further include the shell having a bone engagement surface.

The prosthesis according to the present disclosure may further include the shell having an inner surface defining a first cavity and the liner having an inner surface defining a second cavity, the liner being disposed within the first cavity and the femoral head being disposed within the second cavity.

The prosthesis according to the present disclosure may further include a channel formed in the liner that engages the locking mechanism.

A prosthesis according to various embodiments of the present disclosure may include a cup. An insert may be disposed within the cup. The insert may be deformed and expanded when disposed in the cup. A femoral head may be disposed within the insert such that the femoral head articulates within the insert. A ring may secure the insert within the cup. The ring may be removed when the cup, insert, and femoral head are implanted.

The prosthesis according to the present disclosure may further include walls of the cup extending beyond a hemisphere and walls of the insert extending beyond a hemisphere.

The prosthesis according to the present disclosure may further include the cup having a peripheral surface and a diameter of the peripheral surface being less than a diameter of a hemisphere of the cup. The insert has a rounded edge, and a diameter of the rounded edge is less than a diameter of a hemisphere of the insert.

The prosthesis according to the present disclosure may further include a groove formed in the insert that engages the ring.

A method for implanting a prosthesis according to the present disclosure may include inserting a shell into an acetabular cavity; inserting a liner into a cavity defined within the shell; engaging a locking mechanism in a channel formed in the liner for securing the liner in the shell; inserting a femoral head into a cavity defined within the liner; and removing the locking mechanism from the channel.

The method for implanting a prosthesis according to the present disclosure may further include dislocating a natural femoral head from the acetabular cavity.

The method for implanting a prosthesis according to the present disclosure may further include boring the acetabular cavity in preparation to receive the shell.

The method for implanting a prosthesis according to the present disclosure may further include deforming the liner to insert the liner within the shell.

The method for implanting a prosthesis according to the present disclosure may further include impacting the shell into the acetabular cavity.

The method for implanting a prosthesis according to the present disclosure may further include securing the shell to the acetabular cavity.

The method for implanting a prosthesis according to the present disclosure may further include the locking mechanism preventing the liner from moving during insertion of the femoral head.

The method for implanting a prosthesis according to the present disclosure may further include aligning the shell with the acetabular cavity using a plurality of notches in the shell.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
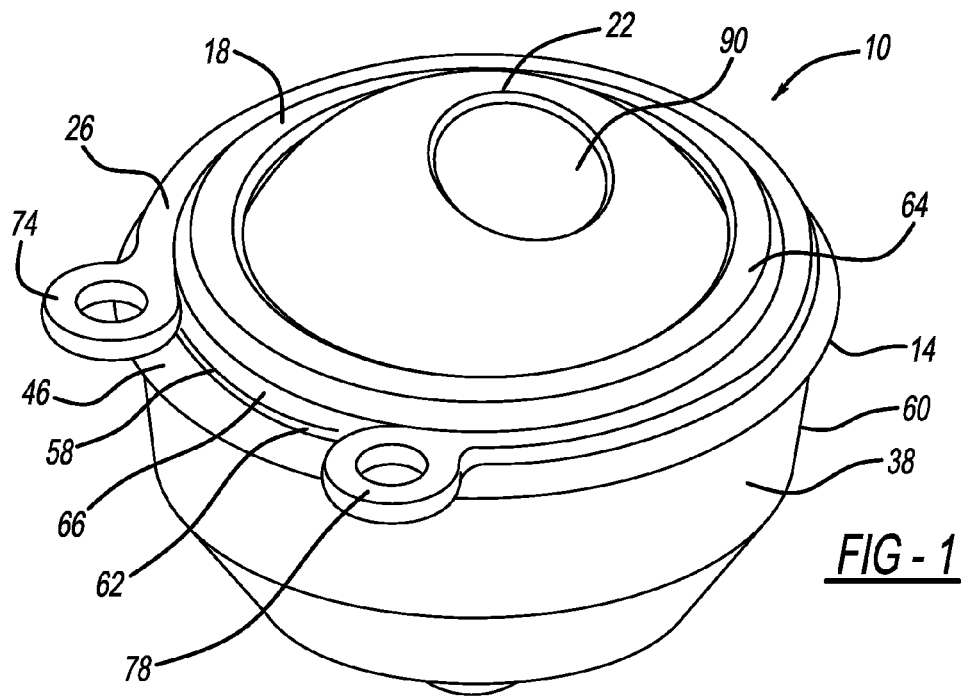
FIG. 1 is a perspective view of an acetabular prosthesis according to the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Further, various features in the specific exemplary embodiments may be combined with other specific exemplary embodiments.

Referring to FIGS. 1-3A, an example embodiment of an acetabular prosthesis 10 according to the present disclosure is shown. The acetabular prosthesis 10 includes a shell or cup 14, a liner or insert 18, a femoral head 22, and a locking mechanism 26, which may include a ring or clip. The shell 14 has an inner surface 30 defining a cavity 34 and an outer surface 38 capable of being coupled or impacted into an acetabular cup (FIG. 6) or directly into a prepared acetabulum 42 (FIG. 4). The shell 14 may further include a button 44 to assist in alignment and fixation in the acetabular cup or prepared acetabulum 42. The button 44 may be a projection extending from the outer surface 38 of the shell 14 along an axis X. The button 44 may be of a rectangular or square shape having rounded corners, may be of a circular or semicircular shape, or may be of any other suitable shape for alignment and/or fixation.

Between the outer surface 38 and the inner surface 30 is a peripheral surface or rim 46. Along the peripheral surface 46, the shell 14 may further include a plurality of notches (not illustrated, but similar to the notches 96 illustrated in FIGS. 5 and 6). The notches may extend along the axis X perpendicular to a plane YZ formed by the peripheral surface or rim 46. The notches may be used to align and/or fix the shell 14 within the prepared acetabulum 42.

The liner 18 may be disposed within the cavity 34 of the shell 14 at a selected time. The liner 18 may include an inner surface 50 defining a cavity 54 for receiving the head 22 and an outer surface 58. The outer surface 58 of the liner 18 may be slideably engaged with the inner surface 30 of the shell 14. The liner 18 may be formed of a polymer, such as, for example, ultra-high molecular weight polyethylene (UHMWPE). The liner 18 is constrained within the cavity 34 such that the liner 18 cannot index over when the acetabular prosthesis 10 is assembled intraoperative. In other words, the liner 18 may not move, such as rotate or slide, out of the shell 14 when the liner 18 is assembled into the shell 14.

As discussed further herein, the liner 18 is configured to move within the shell 14 after positioning the liner 18 within the shell 14. The positioned liner 18 and shell 14, therefore, may be referred to as a dual mobility prosthesis. This may allow a range of motion of a positioned femoral head within the prosthesis greater than if the liner 18 were fixed within the shell 14. Thus, a femur may have a large range of motion. The liner 18 may be fixed, as discussed further herein, from movement relative to the shell 14 during insertion of the femoral head. In other words, the liner 18 may not move or rotate (i.e. index) such that an axis Y through a rounded edge or rim 64 forming an opening into the cavity 54 of the liner 18 may not move relative to the axis X through an edge 35 forming an opening into the cavity 34 of the shell 14.

Walls 60, 62 of the shell 14 and liner 18 may both extend beyond individual hemispheres A and B of the shell 14 and liner 18. This arrangement leads to a dual constraint system and a decreased risk of dislocation of the head 22 from the acetabular prosthesis 10. Further, the arrangement reduces the need for a constraining feature, increasing the range of motion of the head 22 in the liner 18. The liner 18 may extend further beyond the peripheral surface 46 of the shell 14. The rounded edge, or rim, 64 extends between the inner surface 50 and outer surface 58. A channel, or groove, 66 extends annularly in the outer surface 58 below the rounded edge 64, just beyond the peripheral surface 46 of the shell 14.

Because the wall 60 of the shell 14 extends beyond the hemisphere A, a diameter D1 of the peripheral surface 46 of the shell 14 is smaller than a diameter D2 of the hemisphere A of the shell 14. Because the wall 62 of the liner 18 extends beyond the hemisphere B, a diameter d1 of the rounded edge or rim 64 is smaller than a diameter d2 of the hemisphere B of the liner 18. Further, the outer surface 58 at the diameter d2 may be larger than the diameter D1, but smaller than diameter D2 such that the liner 18 fits within the cavity 34 of the shell 14.

Since the diameter D2 may be larger than the diameter D1, the liner 18 cannot be inserted into the shell 14 without deformation. The liner 18 may be deformed by any known method, such as, for example, by shrinking and expanding the liner 18 into the shell 14. In one example, the liner 18 may be shrunk by cooling, for example only, in liquid nitrogen, and then the liner 18 will expand within the shell 14 as the liner 18 warms to room temperature. Alternatively, the liner may be deformed by applying manual pressure to the inner surface 50 of a dome portion 70 of the liner 18 to manually force the liner 18 into the shell 14.

Figure 2:
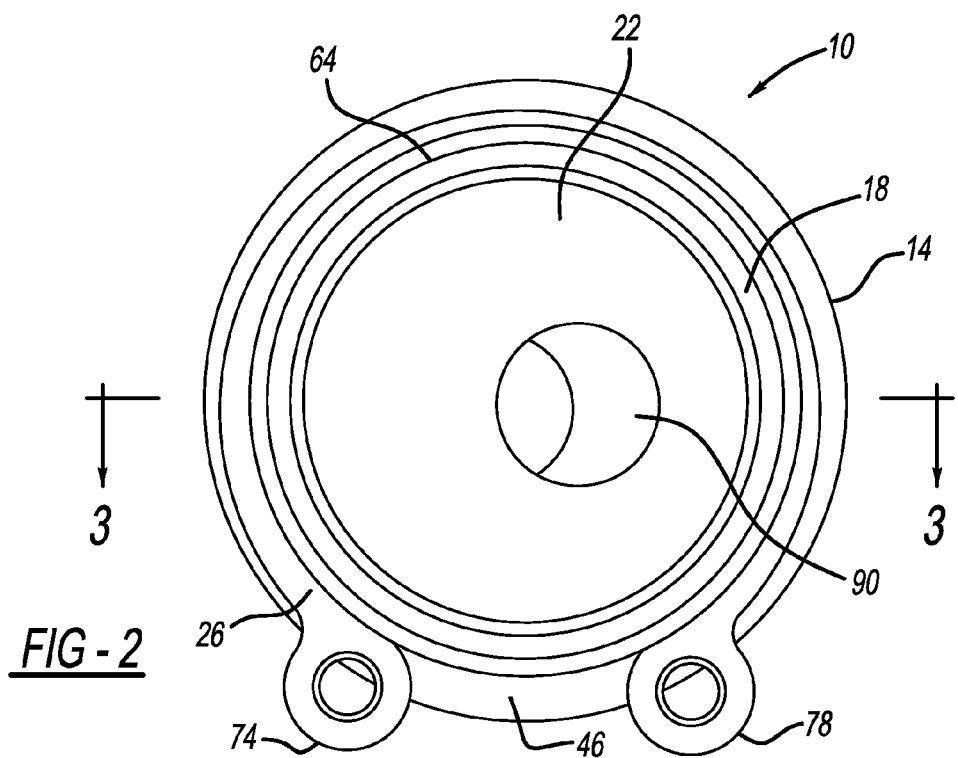
FIG. 2 is a top view of the acetabular prosthesis of FIG. 1.

The locking mechanism 26 is disposed on the peripheral surface 46 and at least partially within the channel 66 of the liner 18 and locks within the channel 66 of the liner 18. The locking mechanism 26 may be of a ring shape and functions to retain the liner 18 within the shell 14. Specifically, the locking mechanism 26 prevents the liner 18 from indexing over, folding over, moving outside of, or sliding out of the shell 14 and thus maintains the orientation of the liner 18 within the shell 14 when the head 22 is inserted into the liner 18. The locking mechanism 26 may include a first end 74 and a second end 78 (FIGS. 1 and 2). It is envisioned that the locking mechanism 26 can be initially expanded and disposed at least partially in the channel 66 of the liner 18. Once in the channel 66, the locking mechanism 26 can contract back to an original configuration, applying pressure to the channel 66 to retain the locking mechanism 26 on the channel 66. The locking mechanism 26 may extend annularly around the liner 18 such that the first end 74 and the second end 78 are either touching or slightly spaced apart. For example, the first end 74 and the second end 78 may be spaced a distance less than half of a circumference of the rounded edge 64 of the liner 18.

The locking mechanism 26 may be formed of a biocompatible metal or polymer, such as UHMWPE. While the locking mechanism 26 is illustrated as a ring, it is envisioned that other locking mechanisms such as screws, snaps, tabs, locking flanges, or other known locking mechanisms may be used to restrain the liner 18 within the shell 14.

The liner 18 functions to constrain the head 22 of a femoral prosthesis 82. The liner 18 constrains the head 22 by extending beyond the hemisphere B of the liner 18. A diameter DH of the head 22 is less than the diameter d2 of the hemisphere B such that the head 22 fits within the cavity 54 defined by the liner 18. The diameter d1 of the rounded edge 64 is less than a diameter DH of the head 22, and therefore, retains the head within the cavity 54. The locking mechanism 26 further restrains the head 22 within the liner 18. Thus, the inner surface 50 of the liner 18 substantially encapsulates the head 22 of the femoral prosthesis 82.

Figure 10:
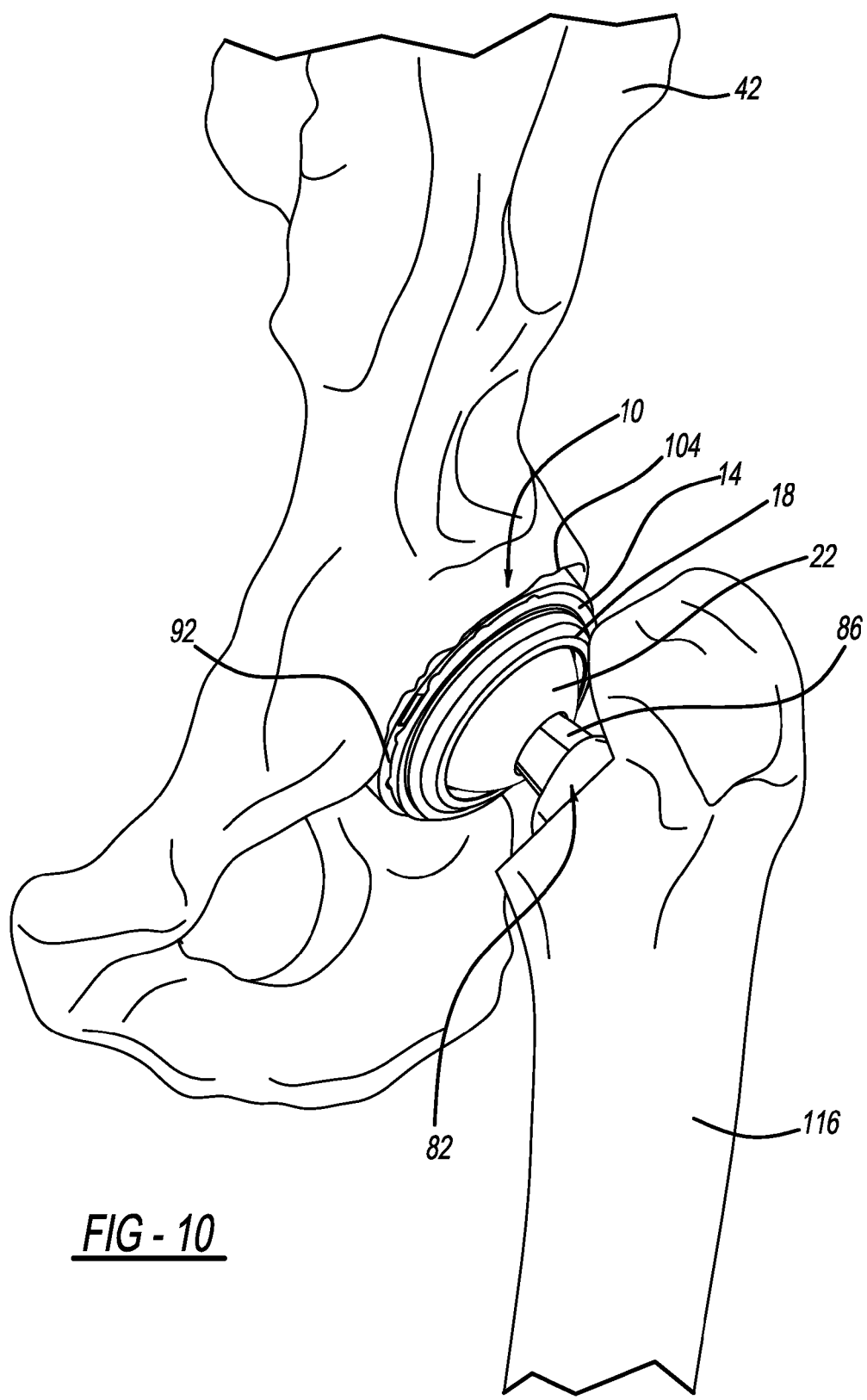
FIG. 10 is an environmental view of the acetabular prosthesis assembled in the acetabulum according to the present disclosure.

Because the shell 14 and the liner 18 both extend beyond their respective hemispheres A and B, the locking mechanism 26 may be removed after all parts of the acetabular prosthesis 10 and femoral prosthesis 82 are implanted (FIG. 10). Because the shell 14 and liner 18 extend beyond their respective hemispheres A and B and because diameter D1 of the shell 14 is smaller than diameter D2 of hemisphere A and diameter d1 of the liner 18 is smaller than diameter d2 of hemisphere B, the shell 14 and liner 18 retain the head 22 within the acetabular prosthesis 10. Thus, an additional locking, such as the locking mechanism 26, is not needed, and as such, locking mechanism 26 may be removed after implantation of both the acetabular prosthesis 10 and the femoral prosthesis 82.

Figure 8:
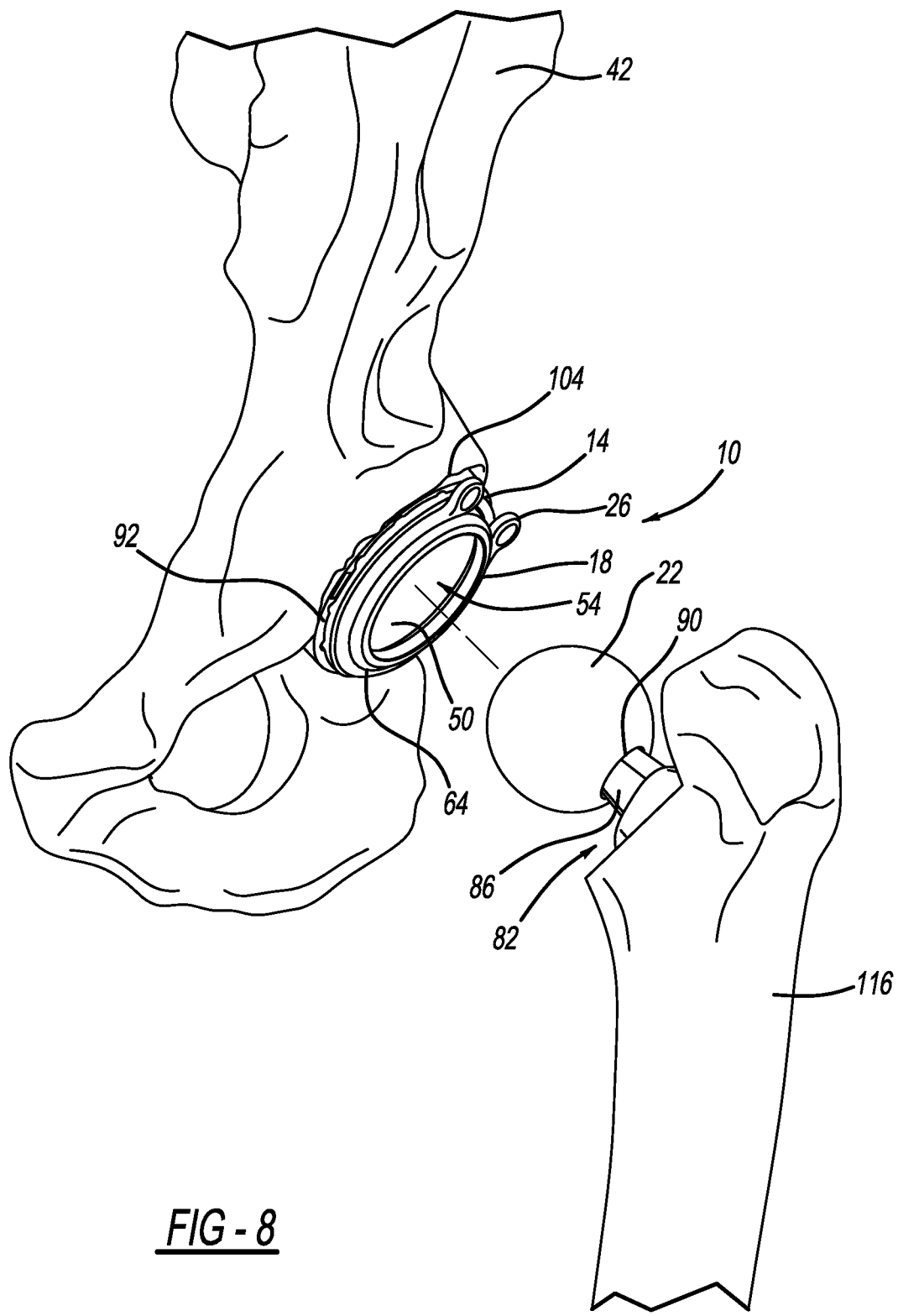
FIG. 8 is an environmental view of a femoral head assembled onto a femoral stem and aligned with the acetabulum and acetabular prosthesis of FIG. 7 according to the present disclosure.

The head 22 may be formed of biocompatible metal, ceramic, or combinations thereof. A stem 86 of the femoral prosthesis 82 may extend into, and be fixed within, a bore 90 within the head 22 (FIG. 8). The stem 86 may be fixed within the bore 90 by adhesive, material deformation, or any known method. The head 22 may be connected to the stem 86, such as via a neck. The head and stem may be any appropriate proximal femoral implant, such as the proximal femoral implant product sold by Biomet, Inc., as the Taperloc® Hip System.

Figure 3A:
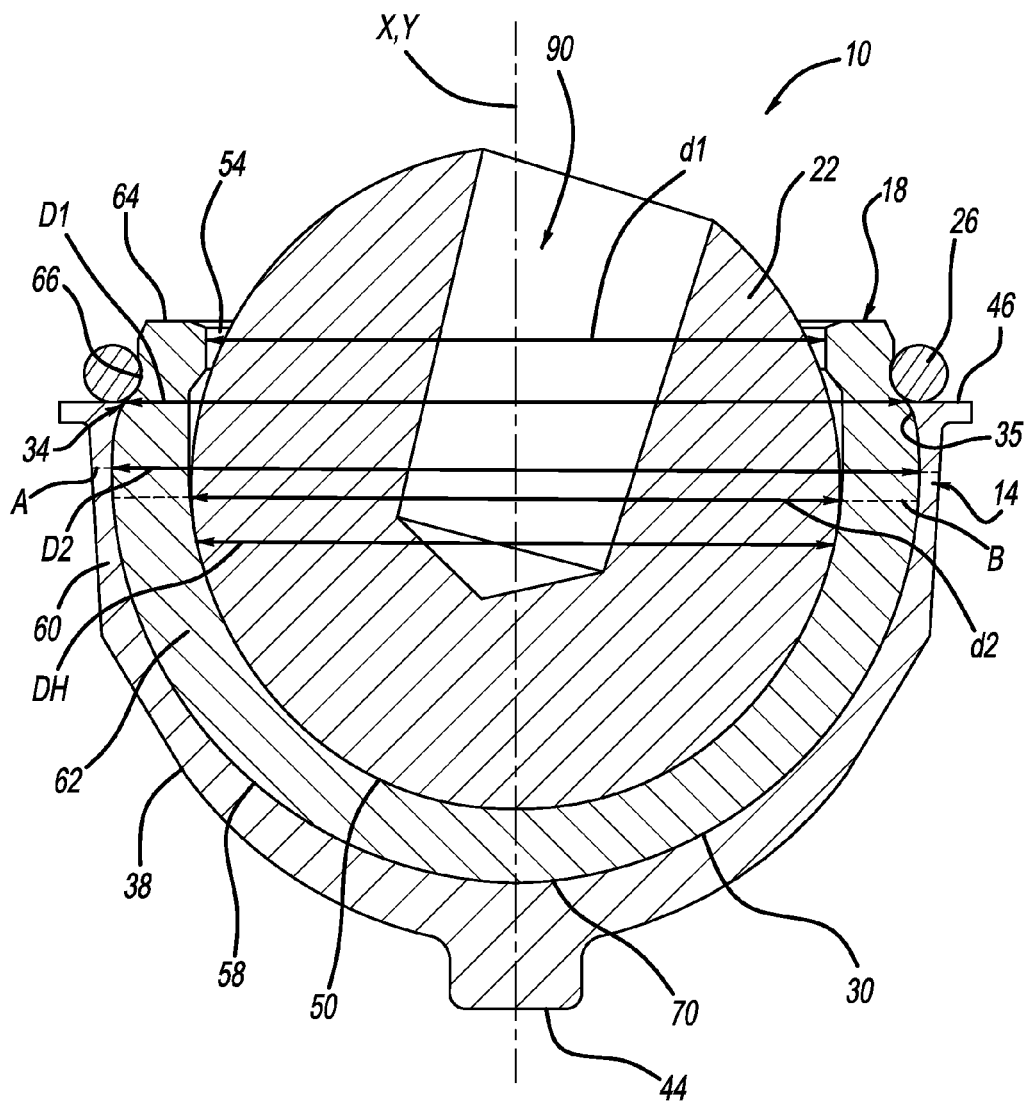
FIG. 3A is a cross-sectional view of the acetabular prosthesis cut at 3-3 in FIG. 2.

As illustrated in FIG. 3A, the acetabular prosthesis 10 may include the shell or cup 14, the liner or insert 18, the femoral head 22, and the locking mechanism 26 and may be inserted into an acetabular cup 92 (illustrated in FIGS. 5-10). The acetabular cup 92 may be similar to the acetabular cup Freedom™ Constrained Liner System, sold by Biomet, Inc. or any other suitable acetabular cup 92. Along a peripheral surface 94, the acetabular cup 92 may include a plurality of notches 96 (illustrated in FIGS. 5 and 6). The notches may extend along an axis X perpendicular to a plane YZ formed by the peripheral surface or rim 94. The notches may be used to align the acetabular cup 92 within the prepared acetabulum 42, and/or the notches may fix the shell 14 within the acetabular cup 92.

Figure 3B:
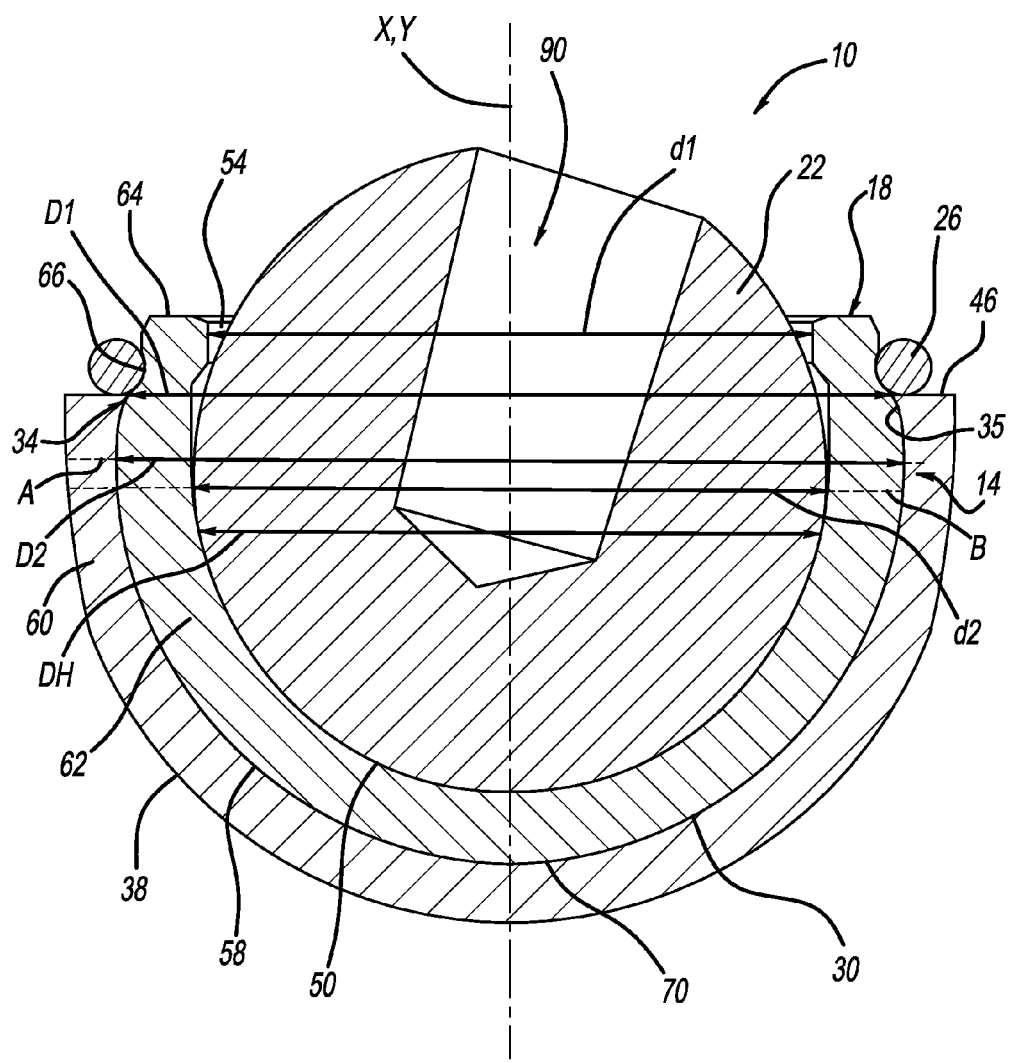
FIG. 3B is a cross-sectional view of an alternative acetabular prosthesis.

In various embodiments, as illustrated in FIG. 3B, the shell 14 may function as an acetabular cup and may be inserted directly into the prepared acetabulum 42 removing the need for an additional acetabular cup. In this embodiment, the outer surface 38 of the shell 14 may be smooth and may not include the button 44 or the rim 46 as described in the embodiment of FIG. 3A. The smooth surface of the shell 14 assists in the fixation of the shell 14 to the prepared acetabulum 42.

The shell 14 may be coupled to the acetabulum 42 by any appropriate known method. Fixation of the shell 14 may include, for example, a plurality of locking projections (not illustrated) for coupling the shell 14 to the prepared acetabulum 42. The shell 14 may also include a plurality of through bores (not illustrated) to receive bone coupling fasteners or screws (not illustrated) to fix the shell 14 to the prepared acetabulum 42. Further, the shell 14 may be formed of a biocompatible metal, and the outer surface 38 may be treated to facilitate bone ingrowth or fixation to bone cement, such as, for example, by porous coating. Further, the outer surface may include or be formed to include pores, such as a porous metal material including Regenerex® porous titanium construct sold by Biomet, Inc.

Figure 4A:
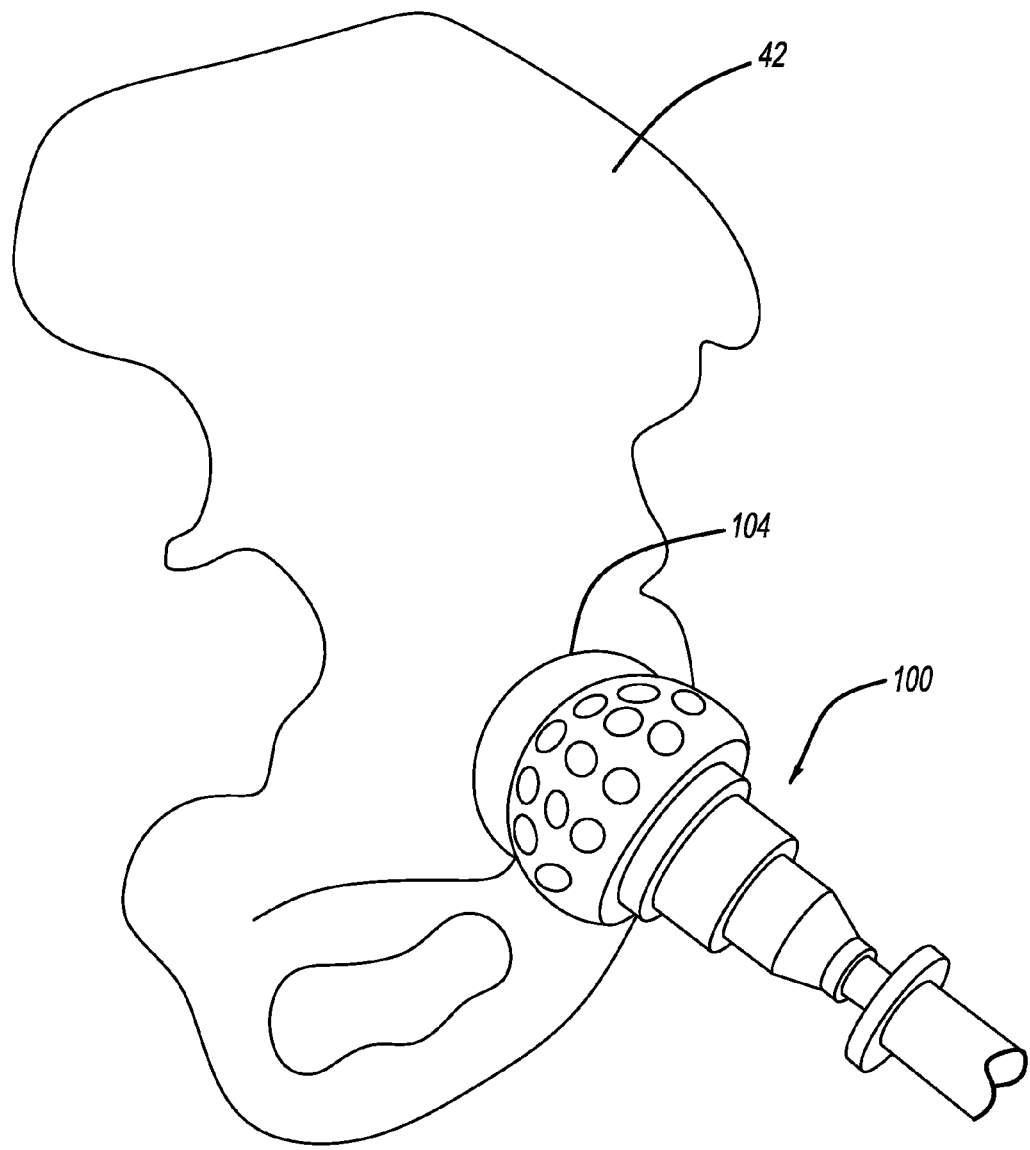
FIGS. 4A and 4B are environmental views illustrating the preparation of an acetabulum according to the present disclosure.
Figure 4B:
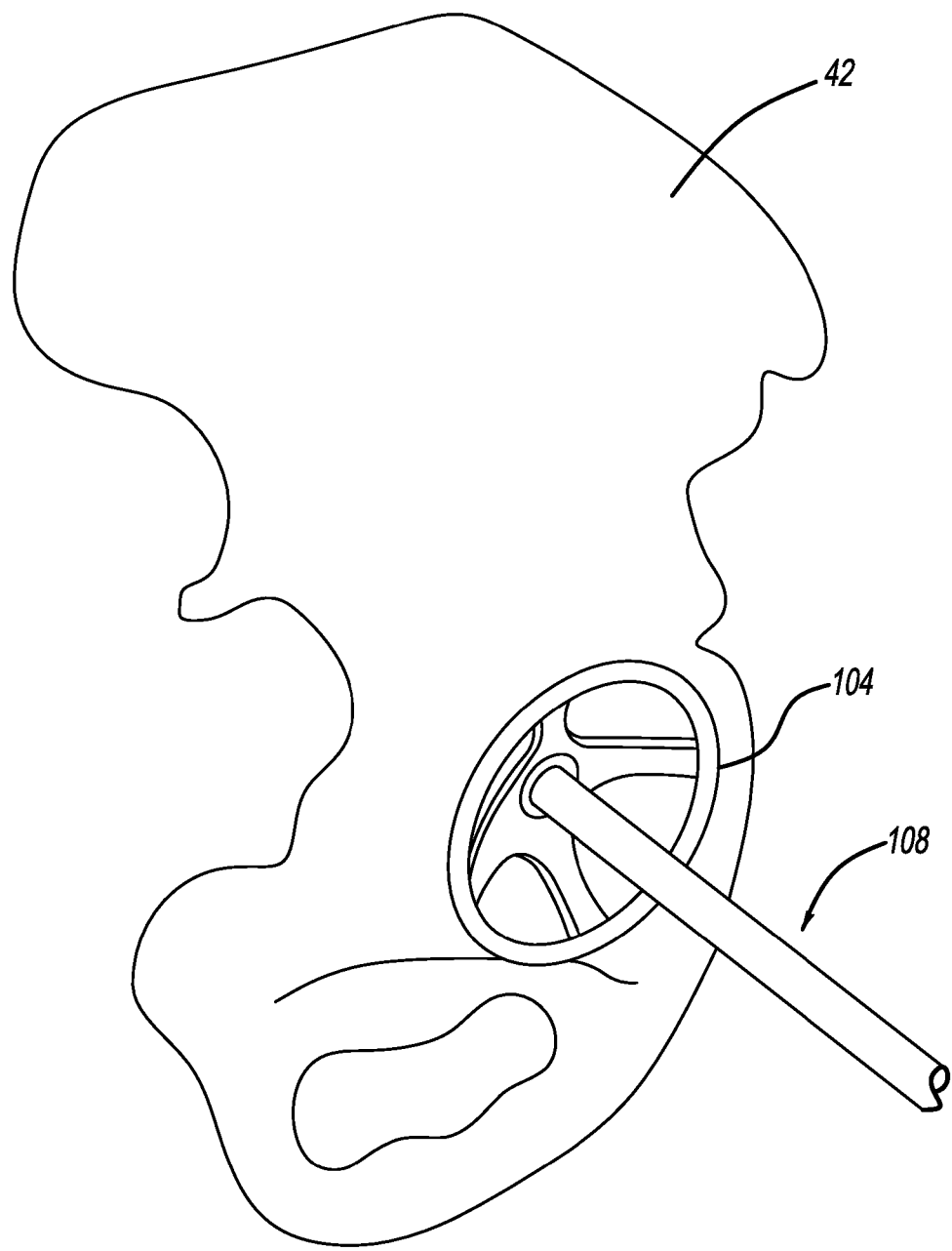

FIGS. 4A-10 illustrate a method for implanting the acetabular prosthesis 10, according to various embodiments. After the natural femoral head (not illustrated) has been dislocated from the acetabulum 42, a bore forming tool 100 is used to enlarge an acetabular cavity 104 for acceptance of the acetabular prosthesis 10, as illustrated in FIG. 4A. It is understood, in various embodiments, that dislocation of the femoral head is not required. In FIG. 4B, an acetabular trial gauge 108 may be used to determine the reaming accuracy and to determine the exterior diameter of the acetabular prosthesis 10 to be used.

Figure 5:
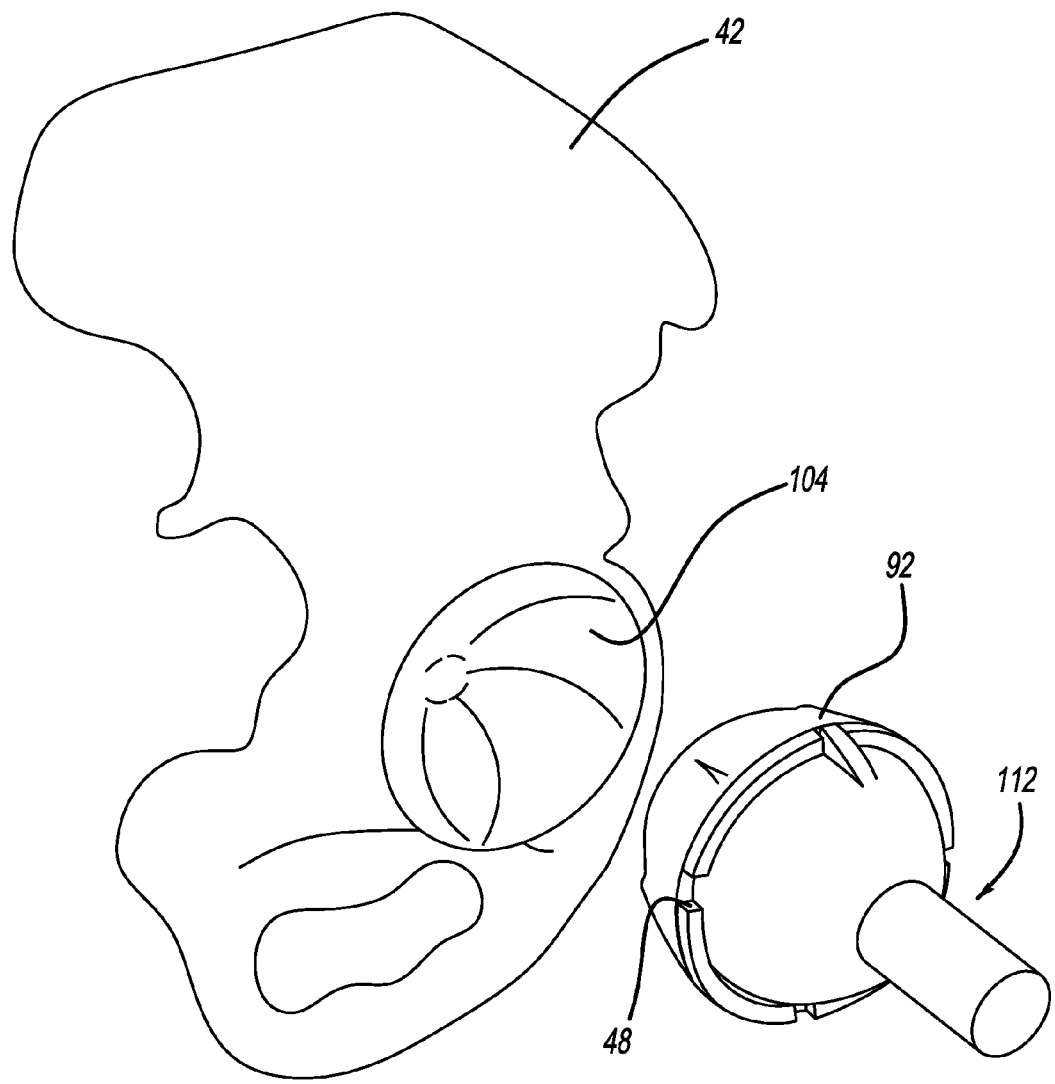
FIG. 5 is an environmental view of an acetabular shell being implanted into the acetabulum of FIGS. 4A and 4B according to the present disclosure.
Figure 6:
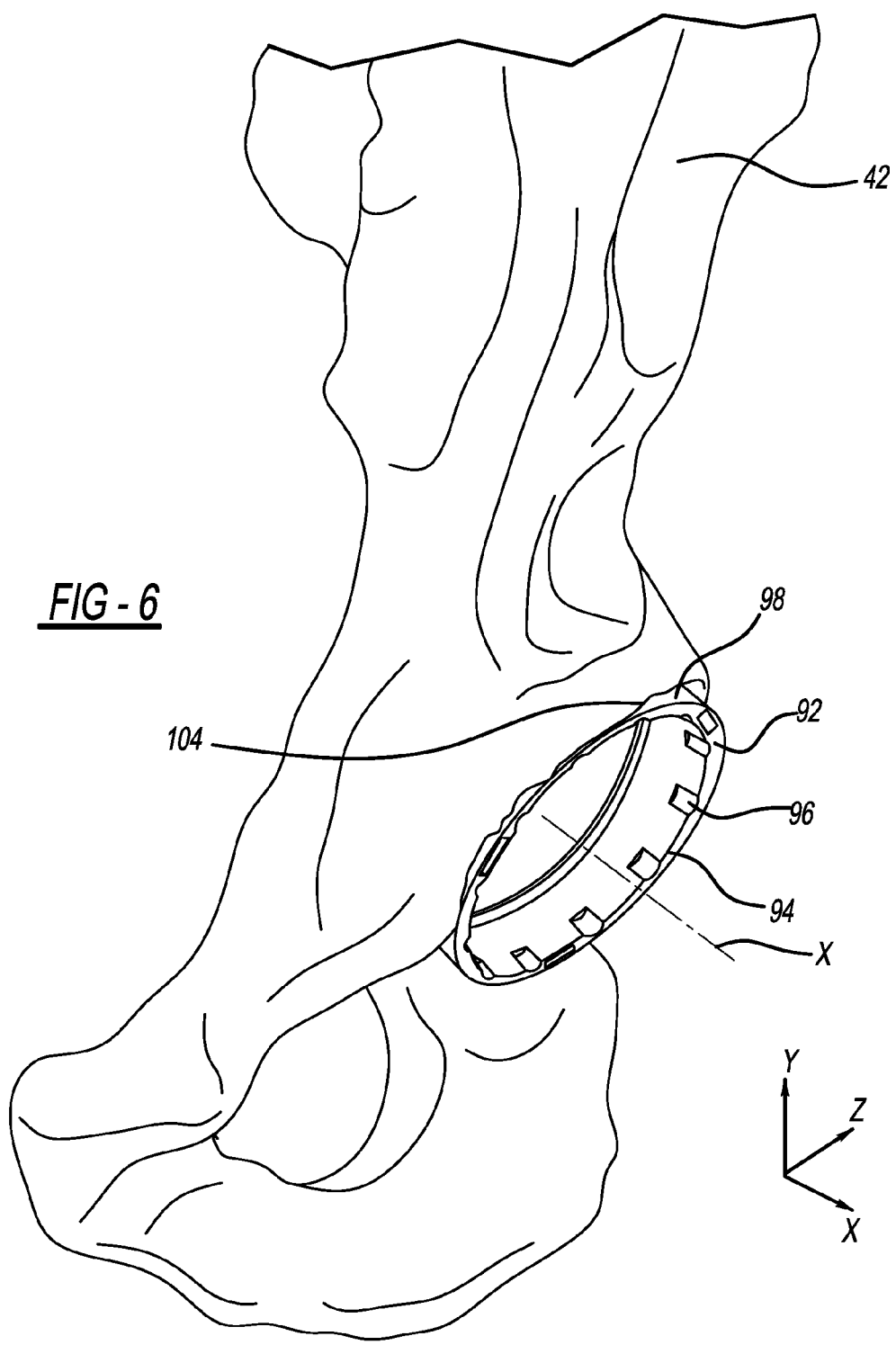
FIG. 6 is an environmental view of the acetabulum of FIGS. 4A and 4B including the acetabular shell according to the present disclosure.

The acetabular cup 92 may be inserted into the prepared acetabulum 42 using an impacting tool 112, as illustrated in FIG. 5. The acetabular cup 92 may be aligned using either a plurality of fixation holes (that will eventually be used to secure the acetabular cup 92 within the acetabular cavity 104) or the plurality of notches 96 disposed on the peripheral surface 94. The acetabular cup 92 may then be impacted into the acetabular cavity 104 and fixed into place. The acetabular cup 92 may be coupled to the acetabulum 42 by any appropriate known method. Fixation of the acetabular cup 92 may include, for example, a plurality of locking projections (not illustrated) for coupling the acetabular cup 92 to the prepared acetabulum 42. The acetabular cup 92 may also include a plurality of through bores (not illustrated) to receive bone coupling fasteners or screws (not illustrated) to fix the acetabular cup 92 to the prepared acetabulum 42. Further, the acetabular cup 92 may be of a biocompatible metal, and an outer surface 98 may be treated to facilitate bone ingrowth or fixation to bone cement, such as, for example, by porous coating. Further, the outer surface 98 may include or be formed to include pores, such as a porous metal material including Regenerex® porous titanium construct sold by Biomet, Inc. Referring specifically to FIG. 6, the prepared acetabulum 42 with the implanted acetabular cup 92 is depicted.

Figure 7:
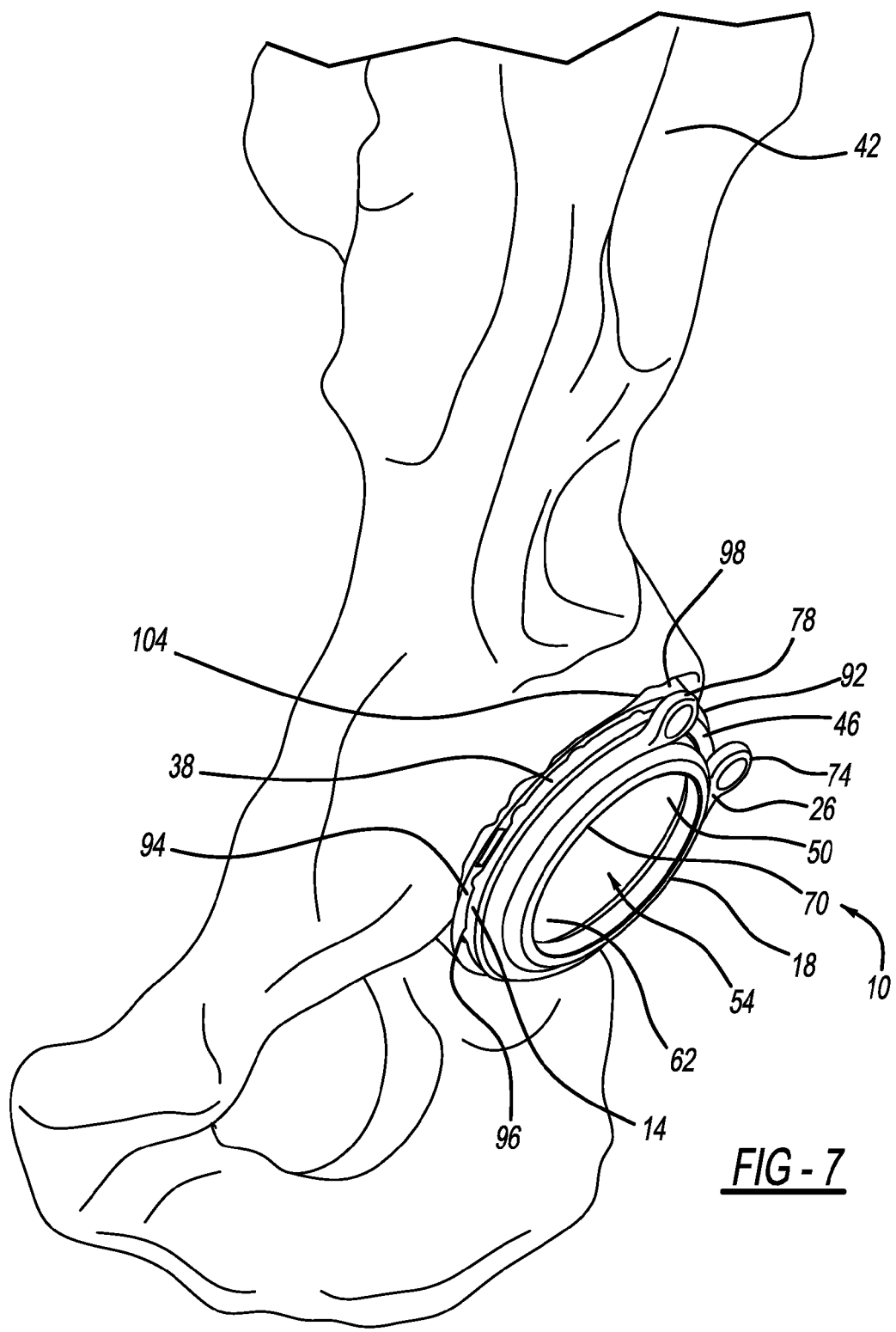
FIG. 7 is an environmental view of the acetabulum of FIGS. 4*a* and 4*b* including the acetabular prosthesis of FIG. 1.

The liner 18 may be inserted into the shell 14 as illustrated in FIG. 7 (also FIGS. 1-3A). As previously stated, the liner 18 may be inserted into the shell 14 by shrinking and expanding the liner 18 into the shell 14 or by applying manual pressure to the inner surface 50 of the dome portion 70 of the liner 18 to manually force the liner 18 into the shell 14. Once the liner 18 is fit within the shell 14 the locking mechanism 26 is expanded and placed within the channel 66 in the liner 18. While it is possible to insert the liner 18 into the shell 14 in the operating room before performing the procedure, this timing may make insertion of the liner 18 into the shell 14 more difficult than inserting the liner 18 into the shell 14 during manufacturing in a controlled environment. For example only, cooling in liquid nitrogen, as previously described, may be difficult in the operating room, thus other insertion methods must be utilized.

In various embodiments, the liner 18 may be pre-fit within the shell 14. During the fabrication process, the liner 18 may be assembled in the shell 14, using methods previously discussed thereby eliminating various procedural steps in the operating room. During assembly, once the liner 18 is inserted in the shell 14, the locking mechanism 26 is expanded and placed within the channel 66 in the liner 18. The complete assembly may then be inserted into the acetabular cup 92 (FIG. 7), during the surgical procedure.

As further illustrated in FIG. 7, the shell 14, liner 18, and locking mechanism 26 may be inserted into the acetabular cup 92. The button 44 of the shell 14 may be aligned with a cylindrical receiving portion (not illustrated) in the acetabular cup 92. The button 44 may prevent the shell 14 from rotating within the acetabular cup 92 and may maintain the orientation of the shell 14 within the acetabular cup 92.

As illustrated in FIG. 8, the head 22 is fixed to the stem 86 of the femoral prosthesis 82, and the femoral prosthesis 82 is implanted into a femur 116. The femoral prosthesis 82 may be implanted into the femur 116 by any known method. The head 22 is then aligned with the liner 18.

Figure 9:
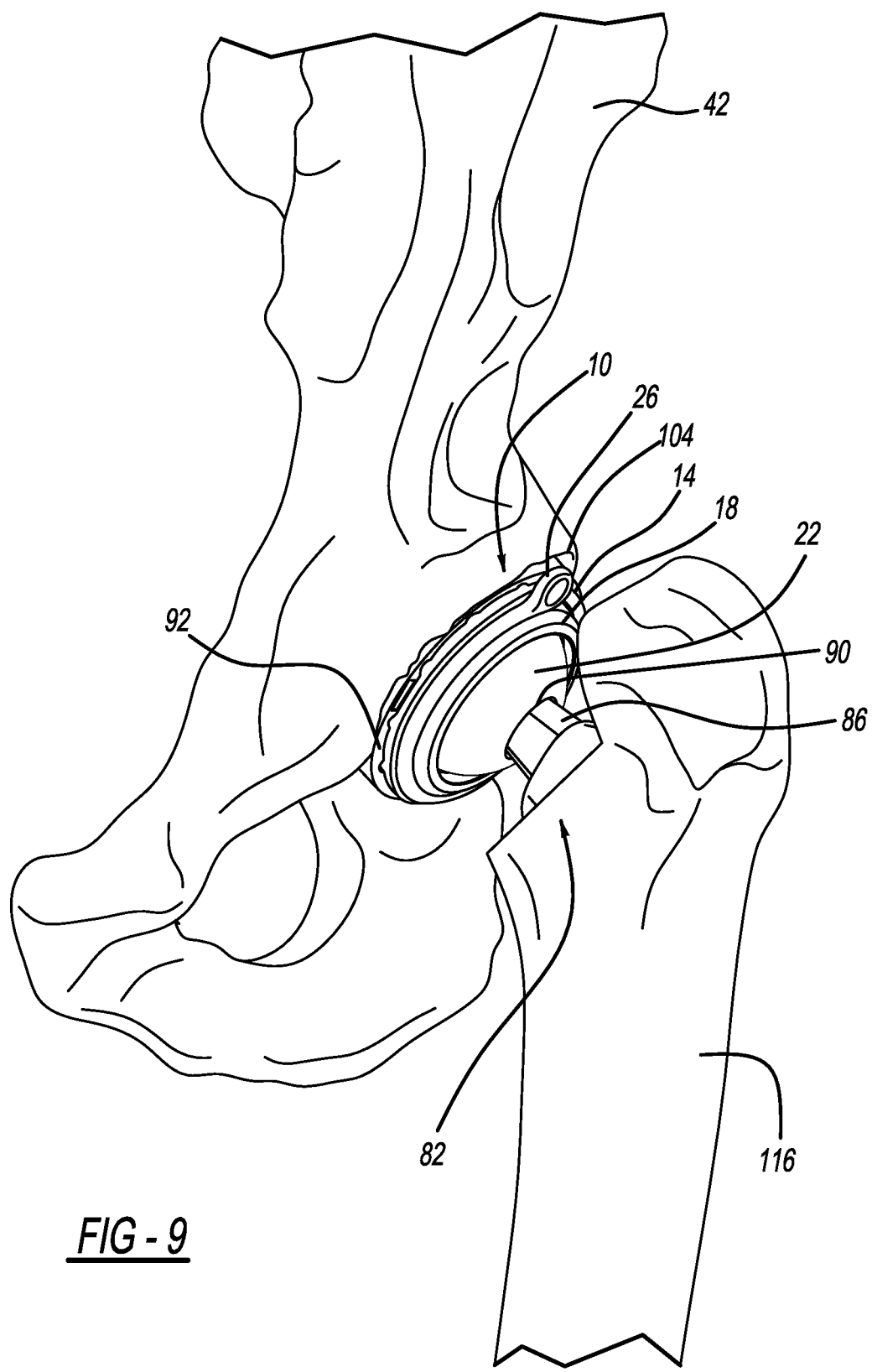
FIG. 9 is an environmental view of the femoral head inserted into the acetabular prosthesis in the acetabulum of FIG. 7 according to the present disclosure.

As illustrated in FIG. 9, the head 22 is inserted into the liner 18 of the acetabular prosthesis 10. In some embodiments, a cylindrical surface may be machined into or onto the head 22, so that the head 22 may be inserted into the liner 18, such as in the Biomet Freedom™ Constrained Liner System, sold by Biomet, Inc. In other embodiments, the head 22 may be pressed into the liner 18 with the aid of a mechanical press tool. The head 22 engages the inner surface 50 of the liner 18 and will articulate within the cavity 54 defined by the inner surface 50 of the liner 18. As the head 22 is inserted into the liner 18, the locking mechanism 26 prevents the liner 18 from indexing over, or moving, such as rotating, out of the shell 14.

Once the head 22 is positioned within the liner 18, the locking mechanism 26 may be removed, as illustrated in FIG. 10. The locking mechanism 26, during insertion of the head 22, maintains or fixes the liner 18 in at least one degree of freedom relative to the shell 14. In other words, the liner 18 is not able to at least move out of alignment of the liner axis X with the shell axis Y. In removing the locking mechanism 26, the liner 18 is freely movable within the shell 14, while being constrained within the shell 14 by the relative geometries of the liner 18 and the shell 14, as discussed above. The movement of the liner 18 within the shell 14, however, increases the range of motion of the head 22 within the shell 14 while maintaining the reduced risk of dislocation of the head 22 from the shell 14.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthesis comprising:
   a shell having a shell inner surface;
   a unitary liner disposed within the shell; and
   a locking mechanism securing the liner within the shell, wherein the locking mechanism is configured to be removed when the shell, liner, and a femoral head are implanted, wherein the shell extends beyond a hemisphere of the shell and the unitary liner extends beyond a hemisphere of the unitary liner, such that an outer liner surface of the unitary liner engages the entirety of the shell inner surface beyond the hemisphere of the unitary liner.

2. The prosthesis of claim 1, wherein the shell includes a peripheral surface and a diameter of the peripheral surface is less than a diameter of the hemisphere of the shell.

3. The prosthesis of claim 2, wherein the liner includes a rounded edge and a diameter of the rounded edge is less than a diameter of the hemisphere of the liner.

4. The prosthesis of claim 3, wherein the diameter of the peripheral surface is less than the diameter of the hemisphere of the liner.

5. The prosthesis of claim 1 wherein the shell is formed of a biocompatible metal and the liner is formed of a biocompatible polymer.

6. The prosthesis of claim 1 wherein the shell includes a bone engagement surface.

7. The prosthesis of claim 1, further comprising:
   the femoral head configured to be disposed within the liner, wherein the shell includes an inner surface defining a first cavity and the liner includes an inner surface defining a second cavity, the liner configured to be disposed within the first cavity and the femoral head configured to be disposed within the second cavity.

8. The prosthesis of claim 1, wherein the liner includes a channel formed in the liner that engages the locking mechanism; and
   wherein the locking mechanism is configured to engage the shell when engaged in the channel to fix the liner relative to the shell in at least one degree of freedom.

9. A prosthesis, comprising:
   a cup having a cup inner surface;
   a unitary insert disposed within the cup, wherein the insert is deformed and expanded when disposed in the cup, the unitary insert including a rim and a hemisphere, wherein a diameter of the rim is less than a diameter of the hemisphere, wherein an outer surface of the insert engages the entirety of the cup inner surface beyond the hemisphere;

a femoral head configured to be disposed within the insert such that the femoral head articulates within the insert; and a ring in a first configuration for securing the insert within the cup, wherein the ring is configured to be removed when the cup, insert, and femoral head are implanted while the femoral head is constrained within the insert.

10. The prosthesis of claim 9, wherein walls of the cup extend beyond a hemisphere of the cup and walls of the insert extend beyond a hemisphere of the insert.

11. The prosthesis of claim 9, wherein the cup includes a peripheral surface and a diameter of the peripheral surface is less than a diameter of a hemisphere of the cup, and the insert rim includes a rounded edge.

12. The prosthesis of claim 9, wherein the insert is moveably constrained within the cup;

wherein the insert includes a groove formed in the insert configured to engage the ring; and wherein the ring when engaging the groove fixes the insert in at least one degree of freedom relative to the cup.

13. A method for implanting a prosthesis, comprising:

inserting a shell including a shell inner surface into an acetabular cavity;

inserting a unitary liner into a cavity defined within the shell, wherein the liner extends beyond a hemisphere of the liner and an outer surface of the liner engages an entirety of the shell inner surface beyond the hemisphere;

engaging a locking mechanism in a channel formed in the liner for at least assisting in securing the liner in the shell;

inserting a femoral head into a cavity defined within the liner; and removing the locking mechanism from the channel.

14. The method of claim 13, further comprising:

dislocating a natural femoral head from the acetabular cavity.

15. The method of claim 13, further comprising:

boring the acetabular cavity in preparation to receive the shell.

16. The method of claim 13, further comprising:

deforming the liner to insert the liner within the shell.

17. The method of claim 16, wherein deforming the liner to insert the liner within the shell includes applying force to a dome of the liner.

18. The method of claim 16, wherein deforming the liner to insert the liner within the shell includes shrinking the liner, inserting the liner within the shell, and expanding the liner to conform to the inside of the shell.

19. The method of claim 13, further comprising:

securing the shell to the acetabular cavity.

20. The method of claim 13, wherein the locking mechanism maintains an orientation of the liner within the shell during insertion of the femoral head.

21. The method of claim 13, wherein removing the locking mechanism from the channel increases a range of motion of the femoral head in the acetabular cavity by allowing free movement of the femoral head within the liner and the liner within the shell.

22. The apparatus of claim 1, wherein the locking mechanism includes a first end defining an aperture and a second end defining an aperture, wherein the first end is configured to be spaced apart from the second end such that a diameter of the locking mechanism can expand.

* * * * *

UNITED STATES PATENT AND TRADEMARK OFFICE
CERTIFICATE OF CORRECTION

PATENT NO. : 9,808,347 B2
APPLICATION NO. : 14/592367
DATED : November 7, 2017
INVENTOR(S) : Bailey et al.

Page 1 of 1

It is certified that error appears in the above-identified patent and that said Letters Patent is hereby corrected as shown below:

In the Claims

In Column 10, Line 29, in Claim 22, delete "apparatus" and insert --prosthesis-- therefor Signed and Sealed this
Twenty-fifth Day of September, 2018

Andrei Iancu
*Director of the United States Patent and Trademark Office*